(12) United States Patent
Danilewitz

(10) Patent No.: US 10,380,543 B2
(45) Date of Patent: Aug. 13, 2019

(54) SYSTEM AND METHOD FOR PHARMACEUTICAL MANAGEMENT AND TRACKING

(71) Applicant: AmerisourceBergen Specialty Group, Inc., Frisco, TX (US)

(72) Inventor: Dale Danilewitz, Haverford, PA (US)

(73) Assignee: AMERISOURCEBERGEN SPECIALTY GROUP, LLC, Frisco, TX (US)

( * ) Notice: Subject to any disclaimer, the term of this patent is extended or adjusted under 35 U.S.C. 154(b) by 642 days.

(21) Appl. No.: 14/738,733

(22) Filed: Jun. 12, 2015

(65) Prior Publication Data

US 2015/0278461 A1    Oct. 1, 2015

Related U.S. Application Data

(63) Continuation of application No. 13/647,737, filed on Oct. 9, 2012, now abandoned, which is a continuation
(Continued)

(51) Int. Cl.
*G06Q 10/08* (2012.01)
*G06K 19/06* (2006.01)
(Continued)

(52) U.S. Cl.
CPC ....... *G06Q 10/087* (2013.01); *G06F 16/9554* (2019.01); *G06F 19/3456* (2013.01);
(Continued)

(58) Field of Classification Search
CPC .... G06Q 10/087; G06Q 10/083; G06Q 30/06; G06Q 30/0635; G06K 7/10366
(Continued)

(56) References Cited

U.S. PATENT DOCUMENTS 4,857,716 A    8/1989   Gombrich et al.
4,866,661 A    9/1989   de Prins
(Continued)

FOREIGN PATENT DOCUMENTS

EP    2272002 A1    1/2011
EP    2382581 A1    11/2011
(Continued)

OTHER PUBLICATIONS

Henri R. Manasse, Kasey Thompson, and Kasey K Thompson. Medication Safety: A Guide for Healthcare Facilities. ASHP: Jun. 15, 2005. Chapter 7: Building an Effective Medication-Safety Team written by May, Sondra.*
(Continued)

*Primary Examiner* — Nathan C Uber
*Assistant Examiner* — Fawaad Haider

(57) ABSTRACT

A product inventory management system including a cabinet configured to contain an inventory of product units having RFID tags and further configured to monitor the inventory by wirelessly detecting the RFID tags, and a server system configured to communicate over a network with the cabinet, the server system capable of managing the inventory of the cabinet. There is also a method for product inventory management, including receiving, in a server system and via a network, inventory data from a cabinet, the inventory data corresponding to an inventory of product units stored in the cabinet, and generating an order to have additional product units added to the cabinet according to the cabinet inventory.

28 Claims, 5 Drawing Sheets

Related U.S. Application Data of application No. 11/607,832, filed on Dec. 1, 2006, now Pat. No. 8,285,607.

(60) Provisional application No. 60/741,631, filed on Dec. 2, 2005.

(51) Int. Cl.
| | |
|---|---|
| G06F 16/955 | (2019.01) |
| G06K 19/07 | (2006.01) |
| G06K 7/14 | (2006.01) |
| G08B 13/24 | (2006.01) |
| G07F 9/02 | (2006.01) |
| G07G 1/00 | (2006.01) |
| G06F 19/00 | (2018.01) |
| G06Q 50/22 | (2018.01) |
| G06K 7/10 | (2006.01) |
| G06Q 30/04 | (2012.01) |
| G16H 40/20 | (2018.01) |

(52) U.S. Cl.
CPC ....... *G06K 7/10366* (2013.01); *G06K 7/1413* (2013.01); *G06K 7/1417* (2013.01); *G06K 19/06037* (2013.01); *G06K 19/0723* (2013.01); *G06Q 10/08* (2013.01); *G06Q 30/04* (2013.01); *G06Q 50/22* (2013.01); *G07F 9/026* (2013.01); *G07G 1/009* (2013.01); *G07G 1/0036* (2013.01); *G08B 13/2434* (2013.01); *G08B 13/2462* (2013.01); *G16H 40/20* (2018.01)

(58) Field of Classification Search
USPC .......................................................... 705/28
See application file for complete search history.

(56) References Cited

U.S. PATENT DOCUMENTS

| | | | |
|---|---|---|---|
| 5,774,053 | A | 6/1998 | Porter |
| 5,936,527 | A | 8/1999 | Isaacman et al. |
| 5,963,134 | A | 10/1999 | Bowers et al. |
| 6,010,064 | A | 1/2000 | Umeda et al. |
| 6,195,645 | B1 | 2/2001 | Itakura et al. |
| 6,249,227 | B1 | 6/2001 | Brady et al. |
| 6,294,999 | B1 | 9/2001 | Yarin et al. |
| 6,323,782 | B1 | 11/2001 | Stephens et al. |
| 6,539,281 | B2 | 3/2003 | Wan et al. |
| 6,629,520 | B2 | 10/2003 | Inagaki et al. |
| 6,707,381 | B1 | 3/2004 | Maloney |
| 6,708,879 | B2 | 3/2004 | Hunt |
| 6,829,520 | B1 | 12/2004 | Green |
| 6,845,909 | B2 | 1/2005 | Bong et al. |
| 6,935,560 | B2 | 8/2005 | Andreasson et al. |
| 6,989,749 | B2 | 1/2006 | Mohr |
| 7,072,855 | B1 | 7/2006 | Godlewski et al. |
| 7,284,704 | B2 | 10/2007 | Lubow |
| 7,406,439 | B2 | 7/2008 | Bodin et al. |
| 7,455,225 | B1 | 11/2008 | Hadfield et al. |
| 7,689,316 | B1 * | 3/2010 | Frederick .............. G06F 19/327 700/231 |
| 7,737,855 | B2 | 6/2010 | Rubinstein |
| 8,095,435 | B2 | 1/2012 | Newton et al. |
| 8,111,159 | B2 | 2/2012 | Andreasson et al. |
| 8,212,677 | B2 | 7/2012 | Ferguson |
| 8,284,059 | B2 | 10/2012 | Ross |
| 8,285,607 | B2 | 10/2012 | Danilewitz |
| 8,738,177 | B2 | 5/2014 | van Ooyen et al. |
| 2002/0029575 | A1 | 3/2002 | Okamoto |
| 2002/0032582 | A1 | 3/2002 | Feeney, Jr. et al. |
| 2003/0117281 | A1 | 6/2003 | Sriharto et al. |
| 2003/0120384 | A1 | 6/2003 | Haitin et al. |
| 2003/0136794 | A1 | 7/2003 | Chirnomas |
| 2003/0144926 | A1 | 7/2003 | Bodin et al. |
| 2003/0186032 | A1 | 10/2003 | Rosenberger et al. |
| 2004/0129779 | A1 | 7/2004 | Kvalheim, Jr. |
| 2004/0186620 | A1 | 9/2004 | Chirnomas |
| 2005/0125097 | A1 | 6/2005 | Chudy et al. |
| 2005/0209934 | A1 | 9/2005 | Irby et al. |
| 2005/0240305 | A1 | 10/2005 | Bogash et al. |
| 2005/0267356 | A1 | 12/2005 | Ramasubramanian et al. |
| 2006/0089858 | A1 | 4/2006 | Ling |
| 2006/0173750 | A1 | 8/2006 | Naley et al. |
| 2006/0192001 | A1 | 8/2006 | Shaffer et al. |
| 2006/0226988 | A1 | 10/2006 | Ernst et al. |
| 2006/0259195 | A1 | 11/2006 | Eliuk et al. |
| 2007/0103304 | A1 | 5/2007 | Newton et al. |
| 2007/0145130 | A1 | 6/2007 | Danilewitz |
| 2007/0150382 | A1 | 6/2007 | Danilewitz |
| 2007/0185615 | A1 | 8/2007 | Bossi et al. |
| 2007/0208595 | A1 | 9/2007 | Ohmura et al. |
| 2007/0272746 | A1 | 11/2007 | Ortiz et al. |
| 2008/0054007 | A1 | 3/2008 | Mador |
| 2008/0128498 | A1 | 6/2008 | Fausak et al. |
| 2008/0223936 | A1 | 9/2008 | Mickle et al. |
| 2009/0287992 | A1 | 11/2009 | Bresolin et al. |
| 2010/0023346 | A1 | 1/2010 | Paty et al. |
| 2010/0042437 | A1 | 2/2010 | Levy et al. |
| 2010/0280840 | A1 | 11/2010 | Fukushi et al. |
| 2011/0187549 | A1 | 8/2011 | Balasingam |
| 2011/0245630 | A1 | 10/2011 | St. Pierre et al. |
| 2012/0004770 | A1 | 1/2012 | Ooyen et al. |
| 2012/0203573 | A1 | 8/2012 | Mayer et al. |
| 2014/0138440 | A1 | 5/2014 | D'Ambrosio et al. |
| 2014/0172651 | A1 | 6/2014 | Flori |
| 2014/0263636 | A1 | 9/2014 | Jones et al. |
| 2014/0288701 | A1 | 9/2014 | Flori et al. |
| 2015/0019251 | A1 | 1/2015 | Flori et al. |

FOREIGN PATENT DOCUMENTS

| | | |
|---|---|---|
| EP | 2430604 A1 | 3/2012 |
| WO | WO 2003/073201 A3 | 9/2003 |
| WO | WO 2004/102492 A2 | 11/2004 |
| WO | WO 2005/015510 A1 | 2/2005 |
| WO | WO 2007/064816 A2 | 6/2007 |
| WO | WO 2007/064899 A2 | 6/2007 |
| WO | WO 2008/000279 A1 | 1/2008 |
| WO | WO 2014/100324 A1 | 6/2014 |

OTHER PUBLICATIONS

International Search Report dated Mar. 27, 2008 in connection with International Application No. PCT/US06/46018; 1 page.
Written Opinion of International Searching Authority dated Mar. 27, 2008 in connection with International Application No. PCT/US06/46018; 5 pages.
International Search Report dated May 6, 2014 in connection with International Application No. PCT/US13/76369; 2 pages.
Written Opinion of International Searching Authority dated May 6, 2014 in connection with International Application No. PCT/US13/76369; 2 pages.
Bielas, W.; "RFID Tags Let Packages Talk"; Aug. 1, 2004; 3 pages.
Brusey, et al.; "Reasoning About Uncertainty in Location Identification with RFID"; IJCAI; Acapulco, Mexico; Aug. 2003; 8 pages.
Collins, J.; "RFID Cabinet Manages Medicine"; RFID Journal; Aug. 12, 2004; 2 pages.
Collins, J.; "Healthy RFID Rivalry for Hospitals" RFID Journal; Aug. 24, 2004; 2 pages.
Floerkemeier, et al.; "Selected Publications" document listing articles disclosed individually; Dec. 18, 2006; 1 pages.
Floerkemeier, et al.; "The Smart Box Concept for Ubiquitous Computing Environments"; Smart Object Conf; Grenoble; May 2003; 4 pages.
Forcinio, H.; "The Business Value of RFID"; Microsoft; Jan. 2006; 19 pages.
Haller, et al.; "The Need for a Universal Smart Sensor Network (White Paper)"; University of Cambridge; Nov. 1, 2002; 24 pages.
Lampe, et al.; "The Smart Box Application Model"; Advances in Pervasive Computing; ACS (OCG); Austria; Apr. 2004; 6 pages.

(56) References Cited

OTHER PUBLICATIONS

O'Connor, M.; "Drug Distributor Uses RFID to Vend Meds"; RFID Journal; 2 pages.
Rogers, M. Ph.D.; "1 to 1 Weekly"; Sep. 20, 2004; 1 page.
Siegemund, et al.; "Interaction in Pervasive Computing Settings Using Bluetooth-Enabled Active Tags & Passive RFID Technology . . . "; IEEE; Mar. 2003; 6 pages.
Siegemund, et al.; "The Value of Handhelds in Smart Environments"; ARCS; Germany; Mar 23-26, 2004; 18 pages.
Smyrlis, L.; "Canadian Transportation Logistics"; Abstract; May 2005; vol. 108, Issue 5; 4 pages.
Swedberg, C.; "RFID Heals Hospital's Inventory Problems"; RFID Journal; Aug. 15, 2005; 2 pages.
Wan, D.; "Magic Medicine Cabinet: A Situated Portal for Consumer Heathcare"; Intl Symposium on Handheld & Ubiquitous Computing; 1999; 4 pages.
Widmer, et al.; "Smart Box Software Framework"; Dec. 18, 2006; 1 page.
Eth Zurich-Swiss Federal Institute of Technology; "The Smart Medicine Cabinet—A Research Demo of the Distributed Systems Group"; May 2003; 2 pages.
"Sirit Partners with Vending Technology and Scopra to Deliver UHF Item Level Tracking Solution"; Las Vegas, Nevada; May 2, 2006; 4 pages.
http://www.mobileaspects.com [first page screenshot]; 1 page.
Petition for Covered Business Method Patent Review of U.S. Pat. No. 8,285,607 Under 35 USC §321.37; Jul. 11, 2014; 85 pages.
Decision on Petition for Covered Business Method Patent Review of U.S. Pat. No. 8,285,607 Under 35 USC §321.37; Jan. 25, 2015; 22 pages.
Defendant and Counterclaim-Plaintiff FFF Enterprises, Inc's Invalidity Contentions; Jun. 16, 2014; 542 pages.
Declaration of Dr. Richard E. Billo, Ph.D.; Jul. 9, 2014; 19 pages.
U.S. Appl. No. 60/724,228, filed Oct. 7, 2005; Michael A. Maloney; 17 pages.
U.S. Appl. No. 60/741,631, filed Dec. 2, 2005; Dale Danilewitz; 26 pages.
U.S. Appl. No. 14/288,139, filed May 27, 2014; Chris Flori, et al.; 42 pages.
Non-Final Office Action dated Dec. 11, 2008 in connection with U.S. Appl. No. 11/607,799; 10 pages.
Non-Final Office Action dated Dec. 29, 2008 in connection with U.S. Appl. No. 11/607,832; 6 pages.
Final Office Action dated Apr. 29, 2009 in connection with U.S. Appl. No. 11/607,799; 10 pages.
Final Office Action dated Jul. 8, 2009 in connection with U.S. Appl. No. 11/607,832; 6 pages.
Non-Final Office Action dated Sep. 1, 2009 in connection with U.S. Appl. No. 11/607,799; 10 pages.
Final Office Action dated Mar. 19, 2010 in connection with U.S. Appl. No. 11/607,799; 14 pages.
Non-Final Office action dated Aug. 26, 2010 in connection with U.S. Appl. No. 11/607,799; 11 pages.
Final Office Action dated Feb. 14, 2011 in connection with U.S. Appl. No. 11/607,799; 15 pages.
Non-Final Office Action dated Jun. 1, 2011 in connection with U.S. Appl. No. 11/607,799; 17 pages.
Final Office Action dated Oct. 7, 2011 in connection with U.S. Appl. No. 11/607,799; 18 pages.
Non-Final Office Action dated Dec. 28, 2012 in connection with U.S. Appl. No. 13/647,737; 6 pages.
Final Office Action dated Aug. 1, 2013 in connection with U.S. Appl. No. 13/647,737; 7 pages.
Non-Final Office Action dated Dec. 20, 2013 in connection with U.S. Appl. No. 13/647,737; 7 pages.
Non-Final Office Action dated Mar. 31, 2014 in connection with U.S. Appl. No. 13/647,737; 8 pages.
Non-Final Office Action dated Jul. 18, 2014 in connection with U.S. Appl. No. 13/647,737; 7 pages.
Non-Final Office Action dated Sep. 9, 2014 in connection with U.S. Appl. No. 13/720,604; 9 pages.
Final Office Action dated Sep. 9, 2014 in connection with U.S. Appl. No. 14/302,127; 9 pages.
Final Office Action dated Nov. 7, 2014 in connection with U.S. Appl. No. 13/647,737; 8 pages.
Final Office Action dated Jan. 28, 2015 in connection with U.S. Appl. No. 14/302,127; 11 pages.
Final Office Action dated Feb. 4, 2015 in connection with U.S. Appl. No. 13/720,604; 11 pages.
International Search Report dated Nov. 23, 2015 in connection with International Patent Application No. PCT/US2015/052686; 5 pages.
Written Opinion of the International Searching Authority dated Nov. 23, 2015 in connection with International Patent Application No. PCT/US2015/052686; 5 pages.
International Search Report and Written Opinion dated Jul. 30, 2015 in connection with International Application No. PCT/US2015/035373; 9 pages.
International Search Report and Written Opinion dated Sep. 30, 2015 in connection with International Application No. PCT/US2015/032730; 8 pages.
Non-Final Office Action dated Jul. 10, 2015 in conection with U.S. Appl. No. 13/647,737; 11 pages.
Non-Final Office Action dated Jul. 30, 2015 in conection with U.S. Appl. No. 14/302,127; 13 pages.
Non-Final Office Action dated Oct. 6, 2015 in connection with U.S. Appl. No. 13/720,604; 14 pages.
Non-Final Office Action dated Oct. 6, 2015 in connection with U.S. Appl. No. 14/738,561; 9 pages.
Non-Final Office Action dated Oct. 7, 2015 in conection with U.S. Appl. No. 14/738,684; 11 pages.
U.S. Office Action dated Mar. 7, 2016 in connection with U.S. Appl. No. 14/498,831, 8 pages.
U.S. Office Action dated Mar. 4, 2016 in connection with U.S. Appl. No. 13/720,604, 14 pages.
U.S. Office Action dated Jan. 25, 2016 in connection with U.S. Appl. No. 14/302,127, 15 pages.
U.S. Office Action dated Jan. 15, 2016 in connection with U.S. Appl. No. 13/647,737, 8 pages.
AmerisourceBergen Specialty Group, Inc. et al., "Final Written Decision", United States Patent and Trademark Office, Before the Patent Trial and Appeal Board, dated Jan. 28, 2016, 37 pgs.
Office Action dated Jul. 22, 2016 in connection with U.S. Appl. No. 13/647,737.
Final Office Action dated Apr. 21, 2016 in connection with U.S. Appl. No. 14/738,684; 11 pages.
Final Office Action dated Apr. 21, 2016 in connection with U.S. Appl. No. 14/738,561; 10 pages.

* cited by examiner

SYSTEM AND METHOD FOR PHARMACEUTICAL MANAGEMENT AND TRACKING

CROSS REFERENCE TO RELATED APPLICATIONS

This application is a continuation of U.S. Non-Provisional patent application Ser. No. 13/647,737 filed Oct. 9, 2012 and entitled "SYSTEM AND METHOD FOR PHARMACEUTICAL MANAGEMENT AND TRACKING," which is a continuation of U.S. Non-Provisional patent application Ser. No. 11/607,832 filed Dec. 1, 2006 and entitled "SYSTEM AND METHOD FOR PHARMACEUTICAL MANAGEMENT AND TRACKING," now U.S. Pat. No. 8,285,607. This application also claims the benefit of the filing date of U.S. Provisional Patent Application No. 60/741,631 filed Dec. 2, 2005 and entitled "SYSTEM AND METHOD FOR PHARMACEUTICAL MANAGEMENT AND TRACKING." The contents of each of these are hereby incorporated by reference into this application as if fully set forth herein.

TECHNICAL FIELD

The present disclosure is directed, in general, to inventory management and tracking systems, and in particular to pharmaceutical management and tracking.

BACKGROUND

Product tracking is of importance to any manufacturing, distribution, or sales enterprise. It can be particularly important in the pharmaceutical area, where many products must be carefully identified and tracked from manufacture until administered to a patient. Typical known means of tracking pharmaceuticals involve manual record keeping and identifying products according to written labels. Inventory management and distribution also typically rely on a manual process of taking a physical inventory of product and manually ordering refills or restocking, while also eliminating product that is nearing or passed its expiry.

Another significant issue with pharmaceuticals is the very high cost of maintaining an inventory of expensive drugs. Some drugs can cost several thousand dollars per dose, and be relatively rarely needed, but these same drugs, when needed, are needed immediately. Pre-purchasing and stocking such drugs is a great expense for pharmacies and hospitals. Further, because of the high cost of these drugs, managing and tracking each product becomes essential.

There is, therefore, a need in the art for improved systems, methods, and apparatuses for inventory management and tracking systems, and in particular for pharmaceutical management and tracking.

SUMMARY

One disclosed embodiment includes a product inventory management system including a cabinet configured to contain an inventory of product units having RFID tags, a reader configured to monitor the inventory by wirelessly detecting the RFID tags, and a server configured to communicate over a network with the cabinet, the server capable of managing the inventory of the cabinet and of maintaining a product inventory list and a consumed product list according to the detected RFID tags.

Another disclosed embodiment includes a method for product inventory management, including receiving, in a server and via a network, data comprising each RFID tag associated with a product unit from a cabinet, the data corresponding to product units stored in the cabinet, creating a current inventory list comprising identifiers corresponding to the plurality of RFID tags, and generating an order to have additional product units added to the cabinet according to the cabinet inventory.

The foregoing has outlined rather broadly the features and technical advantages of the present disclosure so that those skilled in the art may better understand the detailed description that follows. Additional features and advantages of the subject matter of the disclosure will be described hereinafter that form the subject of the claims. Those skilled in the art will appreciate that they may readily use the conception and the specific embodiment disclosed as a basis for modifying or designing other structures for carrying out the same purposes of the present disclosure. Those skilled in the art will also realize that such equivalent constructions do not depart from the spirit and scope of the disclosure in its broadest form.

Before undertaking the DETAILED DESCRIPTION below, it may be advantageous to set forth definitions of certain words or phrases used throughout this patent document: the terms "include" and "comprise," as well as derivatives thereof, mean inclusion without limitation; the term "or" is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, whether such a device is implemented in hardware, firmware, software or some combination of at least two of the same. It should be noted that the functionality associated with any particular controller may be centralized or distributed, whether locally or remotely. Definitions for certain words and phrases are provided throughout this patent document, and those of ordinary skill in the art will understand that such definitions apply in many, if not most, instances to prior as well as future uses of such defined words and phrases.

BRIEF DESCRIPTION OF THE DRAWINGS

For a more complete understanding of the present disclosure, and the advantages thereof, reference is now made to the following descriptions taken in conjunction with the accompanying drawings, wherein like numbers designate like objects, and in which.

DETAILED DESCRIPTION

FIGS. 1 through 5, discussed below, and the various embodiments used to describe the principles disclosed in this patent document are by way of illustration only and should not be construed in any way to limit the scope of the disclosure. Those skilled in the art will understand that the principles may be implemented in any suitably arranged device. The numerous innovative teachings of the present application will be described with particular reference to the presently preferred embodiment.

Various embodiments include a system and method for managing pharmaceutical inventories, and in particular to managing consigned pharmaceuticals in third-party facilities, such as hospital pharmacies. Various embodiments can use a product-management cabinet capable of tracking product inventory, and corresponding products. Before describing overall processes, it will be helpful to discuss various aspects of cabinets and products that can be used in implementing the processes.

Figure 1:
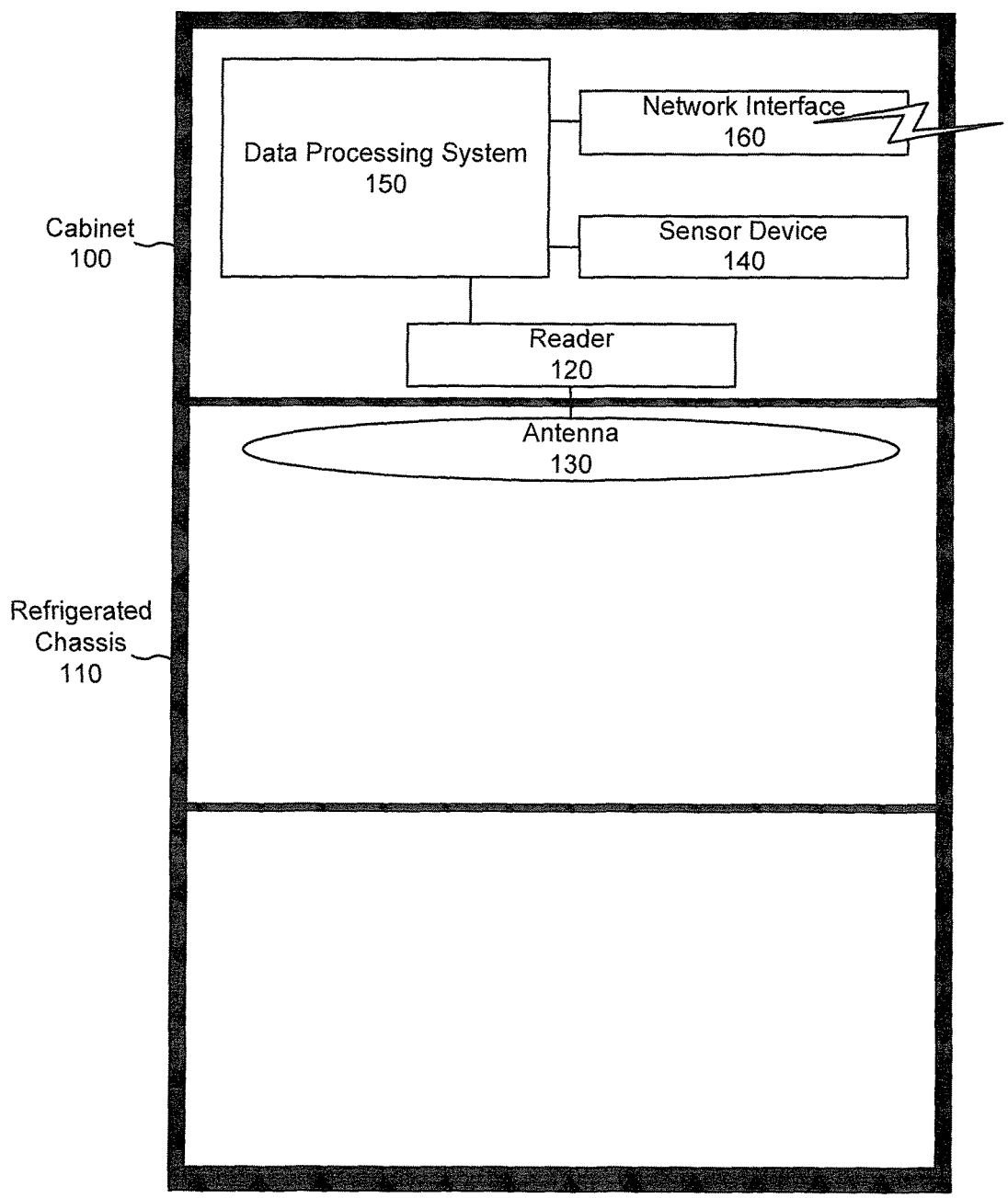
FIG. 1 depicts a simplified block diagram of a cabinet in accordance with an embodiment of the present disclosure.

One aspect of the disclosed embodiments concerns an innovative pharmaceutical cabinet used to store pharmaceutical inventory. FIG. 1 depicts a simplified block diagram of a cabinet that can be used to implement the processes described herein.

The cabinet 100, in a preferred embodiment, includes a refrigerated chassis 110, but can be held at any required temperature, including cooled, frozen, ambient temperature, or even heated, using conventional means. For refrigerated or ambient-temperature use, a conventional refrigerator unit can be modified as described herein to function as the cabinet. For ambient-temperature use, a non-refrigerated cabinet can be used, or the refrigeration unit can be turned off or disconnected. In some embodiments, the cabinet includes a door that is substantially (or at least partially) transparent, or including a window, so that the product unit inventory can be easily viewed without opening the cabinet. The chassis 110 is configured to contain an inventory of product units having RFID tags.

The cabinet 100 also includes a reader 120 to wirelessly and automatically detect and identify the contents of the cabinet. Preferably, this is a radio-frequency identification (RFID) reader, known to those of skill in the art. The cabinet 100 includes one or more RFID antennas 130 connected to RFID reader 120 to scan the contents of the cabinet.

Preferably, the cabinet 100 also includes one or more optional sensor devices 140, such as a thermometer, a door-open sensor; a power-failure sensor and optional backup power supply; a GPS locating device; and other devices, and one or more sensor devices 140 may communicate sensor data to the data processing system described below. In some embodiments, cabinet 100 also has an attached RFID tag.

The cabinet also includes a data processing system 150 capable of communicating with and controlling the RFID reader 120. The cabinet data processing system 150 also includes communications software for communicating as described more fully below. The cabinet data processing system 150 is also preferably connected to communicate with and control the optional sensor devices 140 described above.

Cabinet data processing system 150 can be implemented using any appropriate technology and components, capable of operating as described herein, as known to those of skill in the art. The cabinet data processing system 150 generally includes at least a processor or controller and an accessible memory for storing data as described herein. The data processing system 150 is connected to communicate with the reader 120 and to maintain a product inventory list and a consumed product list according to the detected RFID tags as described herein.

Cabinet data processing system 150 is also connected to communicate with other devices using network interface 160, which can be implemented using wired communications such as Ethernet or a telephone modem, or wireless communications such as GSM or IEEE 802.11, or a cable modem system, or otherwise, or a combination of these. Preferably, network interface 160 communicates using Internet Protocol. Network interface 160 allows the cabinet data processing system 150 to communicate with a server system such as the inventory management system, described below, and optionally with other cabinets 100 using mesh networking, direct cabling, or other technologies known to those of skill in the art. Communications between cabinet data processing system 150 and the inventory management system can be implemented using any suitable data communications technology, or a combination of them. In embodiments where multiple cabinets 100 communicate with each other, these can be configured to communicate with the inventory management system as a single unit with a combined inventory.

Figure 2:
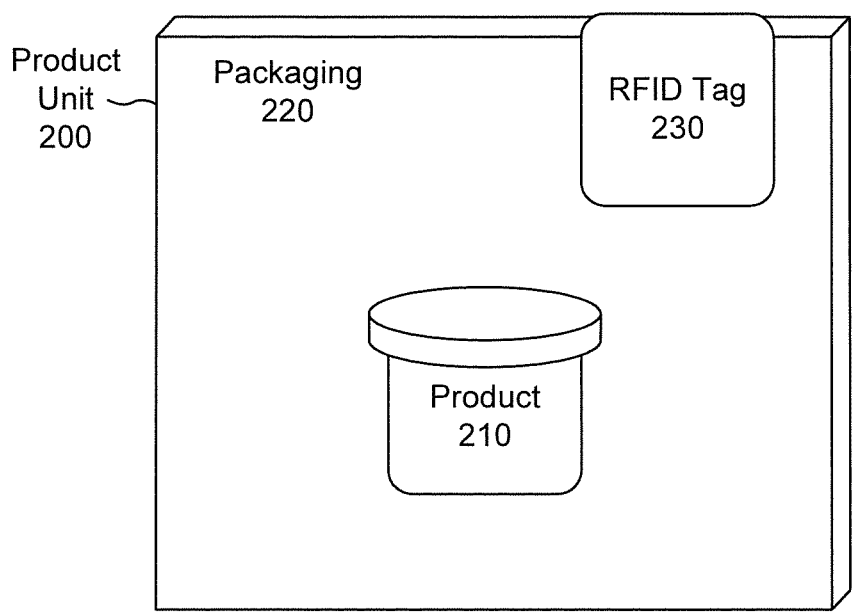
FIG. 2 illustrates a product unit as can be used in various embodiments of the present disclosure.

In use, the cabinet data processing system 150 will make periodic inventory scans, using the RFID reader 120, to uniquely identify each product unit 200 (as shown in FIG. 2) stored in the cabinet. If a new identifier is found during any scan, the cabinet data processing system 150 notes the identifier and stores it to a current inventory list for that cabinet. Similarly, if a specific identifier is no longer detected during a periodic scan, because the product has been removed or the RFID tag has been destroyed, the cabinet data processing system 150 notes the missing identifier and removes it from the current inventory list for the cabinet. The identifiers of such removed products are also stored in a "consumed product" list in the cabinet data processing system.

The product inventory list comprises identifiers corresponding to detected RFID tags. The consumed product list comprises identifiers corresponding to RFID tags previously on the product inventory list that are not detected by the reader either immediately or after a predetermined amount of time.

In this way, the cabinet is configured to monitor the inventory by wirelessly detecting the RFID tags. The cabinet performs a periodic wireless scan to determine the current product units in the inventory, and can determine that a product unit has been removed from the inventory when the RFID tag corresponding to the product unit is not detected for a predetermined amount of time.

Of course, the references herein to the inventory list and consumed product list are not intended to specify a data structure for this information, as this information can be stored in any number of forms within the scope of the disclosed embodiments. "Lists" is simply used for convenient reference.

In alternate embodiments, cabinet 100 can also include a locking mechanism, or one or more individual locking compartments, to control access to the product. These locks can be any known technology, including keylocks, digital keypad locks, biometric locks, etc. Preferably, any locking device can also be opened remotely if the cabinet data processing system 150 receives such a command from the inventory management system.

Cabinet 100 can also include marketing or informational displays, either as a fixed display, or as a customizable electronic display. Similarly, cabinet 100 can include a display connected to cabinet data processing system 150 that is capable of displaying status or informational messages related to the status of the cabinet or the product inventory.

Preferably, cabinet 100 includes a power-failure detection device and a backup power supply. When a power failure is detected, cabinet 100 can sound an audible alarm, and can communicate with the inventory management system to notify it of a problem.

Product: In a preferred embodiment, the product consists of packaged pharmaceuticals, but of course the systems and methods described herein can be applied to other products. FIG. 2 shows a simple illustration of a product unit 200 as can be used in various embodiments of the present disclosure. An important feature of the products, in a preferred embodiment, is that each product unit 200 includes an RFID tag 230 affixed to the product or its packaging, where the RFID tag 230 includes identifying information capable of being read by the RFID reader.

In a typical implementation, an individual product unit 200 includes the product 210 itself in an appropriate packaging 220, such as a box. The packaging includes the RFID tag 230, which seals the package. The RFID tag has at least a unique identifier, such as a serial number, that can be read by the RFID reader. Preferably, to open the package 220 to use the product 210, the RFID tag 230 is destroyed, at which point it can no longer be read by the RFID reader.

For ease of reference, the term "serial number" will be used herein to refer to the unique identifier, although those of skill in the art will recognize that any other style of unique identifier can be used.

As will be understood by those of skill in the art, the product unit 200 represents a generic product. There can be one or more actual products 210 identified as a product unit 200, and preferably packaged together. For example, in the pharmaceutical context, a single dose, pill, or pre-filled syringe can be a single product 210, but multiple ones of these can be packaged together as a single product unit 200, depending on the requirements for using, dispensing, or billing for the product 210.

Figure 3:
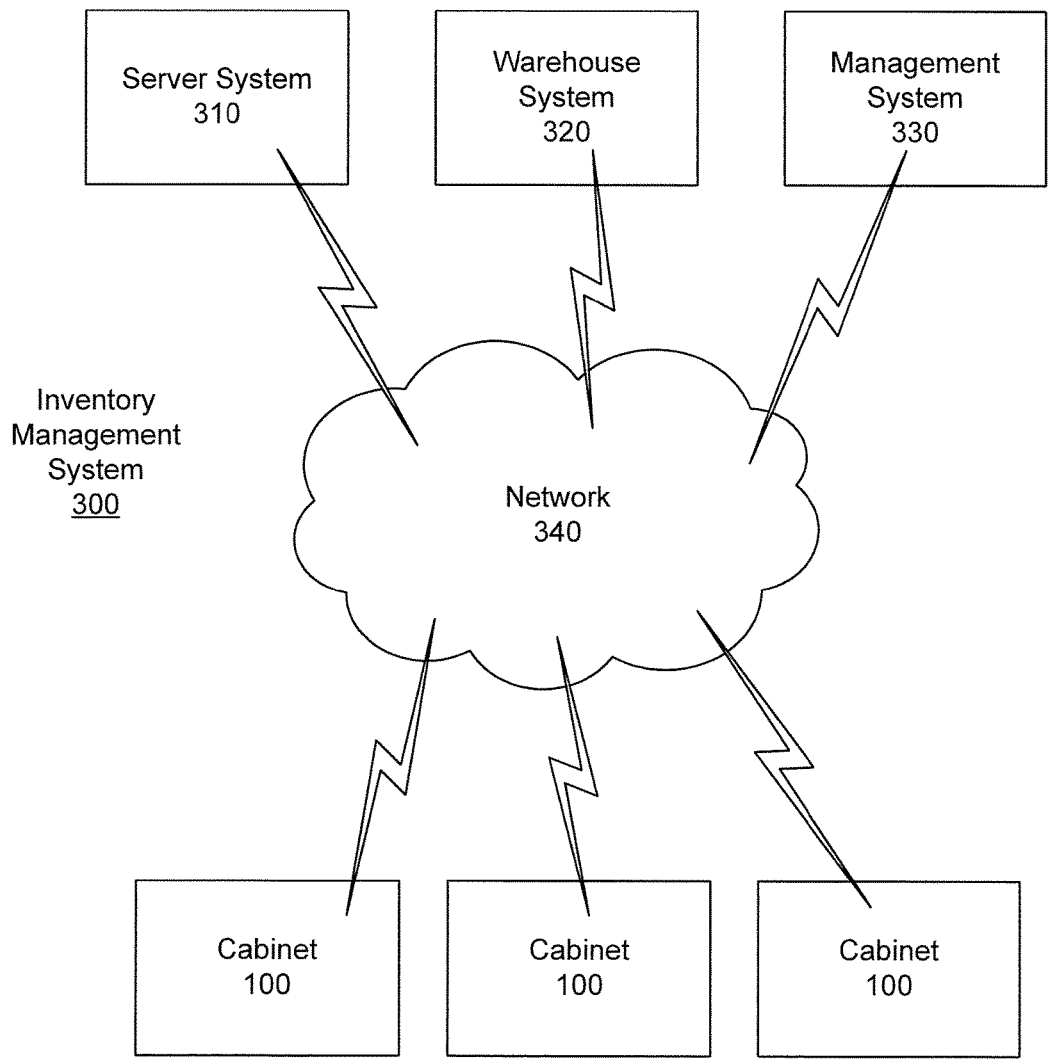
FIG. 3 depicts a simplified diagram of an inventory management system in accordance with an embodiment of the present disclosure.

Inventory management system: An inventory management system 300 is used to control the inventory in multiple cabinets 100. FIG. 3 depicts a simplified diagram of an inventory management system 300, in accordance with an embodiment of the present disclosure, including server system 310, warehouse system 320, management system 330, and multiple cabinets 100, all communicating via network 340. Network 340 can be implemented using any known networking technology, as a public or private network or as direct communications, and is preferably implemented using the Internet to communicate between each system. Network 340 can be implemented using multiple technologies, and can be implemented using multiple separate networks.

Server system 310, warehouse system 320, management system 330, while depicted as single, individual systems in this simplified figure, can each be implemented using one or more data processing systems, which can be commonly located but are not necessarily so. For example, as known to those of skill in the art, different functions of server system 310 may be more efficiently performed using separate data processing systems, each performing specific tasks but connected to communicate with each other in such a way as to together perform the functions described herein for the server system 310 as a whole. Similarly, one or more of server system 310, warehouse system 320, and management system 330 could be implemented as an integrated system as opposed to distinct and separate systems.

Server system 310 performs overall inventory management functions for multiple cabinets 100, as described in more detail below with regard to the overall process. In general, server system 310 communicates with cabinets 100 to monitor the inventory of each cabinet 100 on a regular basis. Server system 310 can also monitor other status information of each cabinet 100 according to sensor devices 140. Server system 310 includes a database of the current inventory of each cabinet 100, the product inventory assigned to each cabinet 100, and other information regarding the cabinets 100.

Server system 310 also tracks all product units 200 from time of purchase and receiving into a warehouse, to shipment placement in a cabinet 100, to storage in cabinet 100, to removal from cabinet 100. Server system 310 will periodically receive communications from each cabinet 100 including the current inventory list, the consumed product list, and other information. These communications can be initiated by server system 310, by polling each of the cabinets 100, or can be initiated by the cabinets 100.

Server system 310 preferably includes a web server interface to allow management using a standard web browser interface. Preferably, at least some data sent and received by server system 310 is in XML format. Server system 310 maintains at least one database for product inventory data; in a preferred embodiment, this database is an SQL database.

Server system 310 can also generate billing and invoice data according to the reports from cabinets 100 of product units 200 that are delivered (added to the current inventory list) or consumed (added to the consumed inventory list).

In various embodiments, the server system 310 is capable of creating an order to have additional product units added to the cabinet according to the cabinet inventory. In some cases, the product units in the cabinet inventory are consignment product units, and the server system 310 creates an invoice when the product units are removed from the inventory. The server system 310 is further capable, in some embodiments, of receiving cabinet status data from the cabinet, and sending cabinet control instructions to the cabinet. The server system 310 is further capable, in some embodiments, of analyzing product consumption data according to inventory data received from the cabinet, as described below.

Warehouse system 320 is connected to communicate with server system 310. Warehouse system 320 is configured to receive inventory management orders from server system 310, to have inventory shipped or delivered for placement in a cabinet 100. Warehouse system 320 is also preferably capable of reading the RFID tags of the product units 200 to identify exactly which product units are being shipped to a given destination. In alternate embodiments, warehouse system 320 is also configured to produce RFID tags for labeling product units 200.

Management system 330 is preferably a data processing system configured to connect with server system 310 to allow a user to manage the functions of server system 310 and the processes it controls. Management system 330 can preferably be implemented using a common data processing system including a standard internet browser, connected to allow the user to connect to a web server interface on server system 310.

Figure 4:
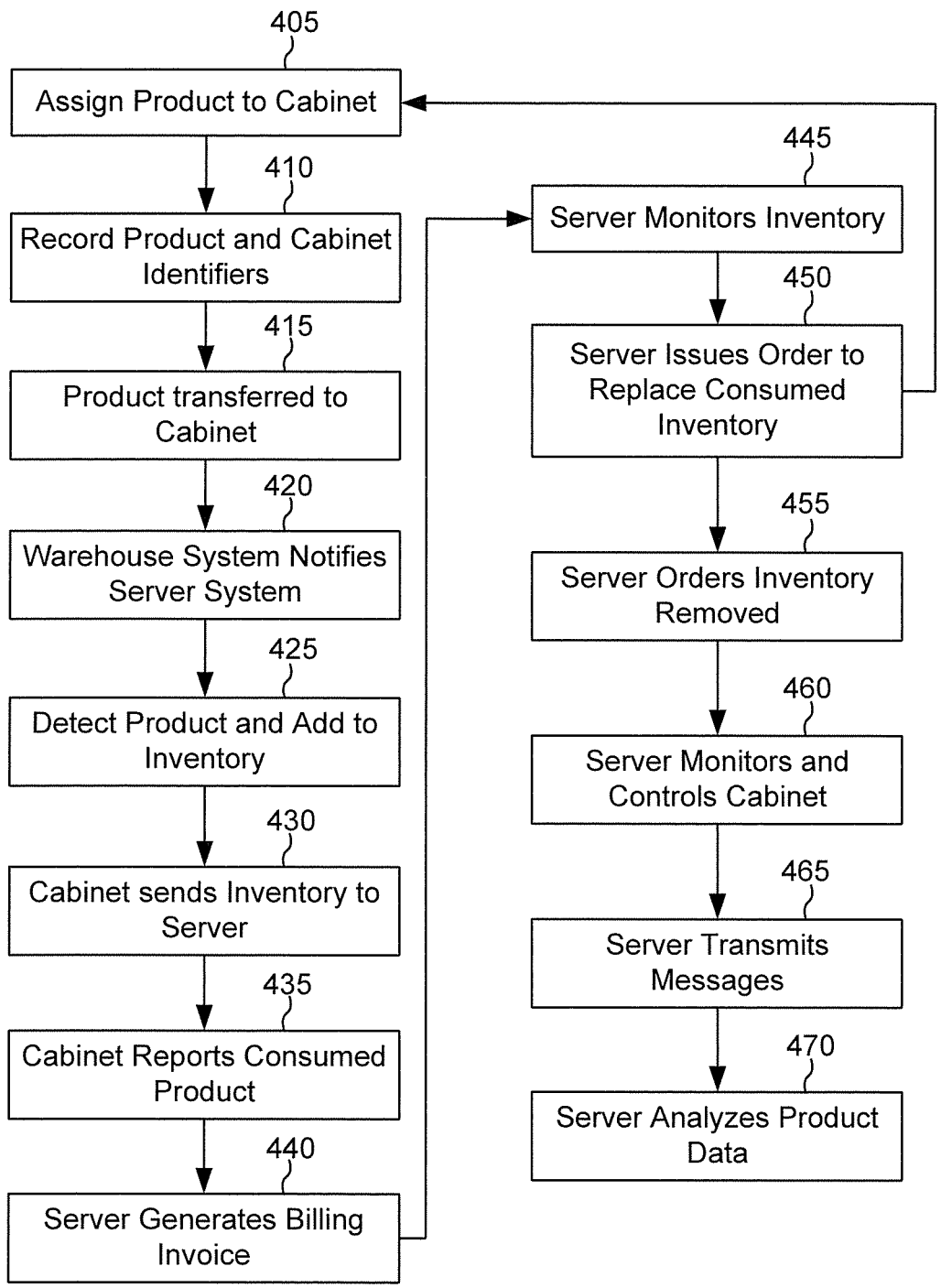
FIG. 4 depicts a flowchart of a first process in accordance with a disclosed embodiment.

FIG. 4 depicts a flowchart of a first process in accordance with a disclosed embodiment. Various embodiments include an inventory management process that provides monitoring, tracking, and billing functions for product units 200 in cabinets 100. In this way, each cabinet 100 can function as a "virtual warehouse" of product units 200 located at each product location, such as hospital pharmacies. This process is particularly useful when the product is not sold when shipped for placement in a cabinet, but rather is held on consignment in the cabinet, and considered sold when removed from the cabinet or the product packaging.

In particular, the embodiments described herein can be used for high-dollar injectable pharmaceuticals, which a pharmacy may desire to have readily available but may not be willing or able to pre-purchase. In this case, the consignment product in the "virtual warehouse" cabinet functions to answer a significant and immediate need in the industry.

According to one process, product units 200 are first designated to be transferred from a warehouse to a cabinet 100 (step 405). Of course, this process is performed for any number of cabinets 100, but for simplicity of description, the process will be described with reference to only one cabinet 100.

The warehouse system 320 will record the serial numbers of each product unit shipped to the cabinet 100, along with an identifier of cabinet 100 (step 410), which may be the RFID tag serial number of the cabinet 100, if it were so tagged. Warehouse system 320 can preferably record each of these serial numbers by performing an RFID scan of all product units being shipped to the cabinet 100.

When the product units are shipped (step 415), warehouse system 320 will notify server system 310 that the product units 200 have shipped, the destination cabinet 100 of the product units 200, and the serial numbers of the RFID tags of each of the shipped product units 200 (step 420), and any other inventory management data.

Server system 310, in turn, periodically communicates with cabinet 100. At some point after shipment, the shipped product units 200 will be delivered to and placed within cabinet 100 at a customer site. Cabinet 100 will detect the serial numbers of the RFID tags of each of the product units, and add those to the current inventory list (step 425). Cabinet 100 will communicate the current inventory list to server system 310, which will update a status record for each corresponding serial number (step 430).

In implementations where there is a direct sale of the product, server system 310 can generate a billing invoice for the customer either when the product units 200 are shipped or when they are detected within cabinet 100, depending on the terms of the customer contract, or at another appropriate time (step 440, see also below).

When the cabinet 100 no longer detects a given RFID serial number of a product unit 200, that serial number is added to the consumed product list and eventually reported to server system 310, as described above (step 435). Typically, this will be when the product unit 100 is opened and the product is consumed, but it can also happen when the RFID tag is destroyed when the packaging is opened, or if the product is otherwise removed, stolen, destroyed, etc.

In a preferred embodiment, a particular product unit is not moved to the consumed product list immediately when it is not detected, but only when it has not been detected for a significant period, such as 24, 48, or 72 hours. This is to accommodate the event that the product unit 200 is removed from cabinet 100 in anticipation of use, but is not actually consumed, and so is returned to the cabinet 100 and is thereafter detected by cabinet 100.

In an implementation where the product is in the cabinet on consignment, server system 310 can generate a billing invoice for the customer when the product units 200 are placed on the consumed product list (step 440).

Server system 310 continues to monitor the inventory of cabinet 100 on a periodic basis. As products are consumed, server system 310 updates its inventory and performs any necessary billing procedures (step 445).

When server system 310 determines that the number of product units 200 in cabinet 100 for a given product has fallen below a predetermined threshold, server system 310 will preferably send a purchase order (for direct sales) or transfer purchase order (for consignment sales) to warehouse system 320 (step 450). Warehouse system 320 will process a new delivery of the required product to the cabinet (e.g., returning to step 405). That is, when the server system determines that a cabinet is running low on a specific product, it will preferably automatically generate an order for the warehouse system to replenish the supply.

Also, in preferred embodiments and particularly in pharmaceutical implementations, the server system 310 will maintain pedigree and expiry information for each product unit 200, associated with the product unit serial number. In the event of a product recall or product that is nearing its expiration in a cabinet, the server system 310 can produce an order for the product to be removed or replaced in the cabinet (step 455), and adjust its inventory and billing records when the replacement is reported by the cabinet.

In alternate embodiments, the temperature and other parameters of the cabinet 100 can be directly modified by cabinet data processing system 150. Further, server system 310 can send appropriate commands to cabinet data processing system 150 to change the cabinet parameters. In this way, for example, server system 310 can determine the optimal cabinet parameters according to the current cabinet inventory, and thereafter modify the parameters accordingly (step 460).

Server system 310 can also track product units 200 indicated as shipped by warehouse system 320 but that are not timely detected by the destination cabinet 100. When this occurs, server system 310 can send an appropriate notice to an operator, the customer, or other appropriate person or system. By reference to the status information of the carrier contracted to deliver the product units, server system 310 can also determine whether the product was delivered to the customer location but never placed by the customer in the cabinet 100. According to the provisions of a customer contract, server system 310 can optionally automatically bill the customer for such product units that are never placed in the destination cabinet.

According to other embodiments, server system 310 can also communicate with physicians and other individuals using electronic mail, text messaging to mobile telephones or PDAs, paging, or in other ways known to those of skill in the art (step 465). These communications can be real-time, such as text messaging or paging, or can be delayed. In particular embodiments, these messages can be used to provide updates of product inventory to individuals regarding the particular cabinets in their facility, to advise of new stock or to warn of low product inventory. These messages can be combined with advertisement or promotional material, for example to promote the use and benefits of particular products stocked or available to be stocked in the cabinet.

In other embodiments, product inventory data can be analyzed and/or aggregated by server system 310 (step 470) in order to determine and predict product usage trends. For example, in the pharmaceutical context, server system 310 can determine the general rate at which any particular product is used in a particular cabinet, and thereby determine an optimum inventory level for that product to meet ongoing and emergent needs. Further, server system 310 can use aggregate data to determine how much product should be ordered and stocked in warehouses, and to determine what drugs are most often used and in what contexts, among other information.

Figure 5:
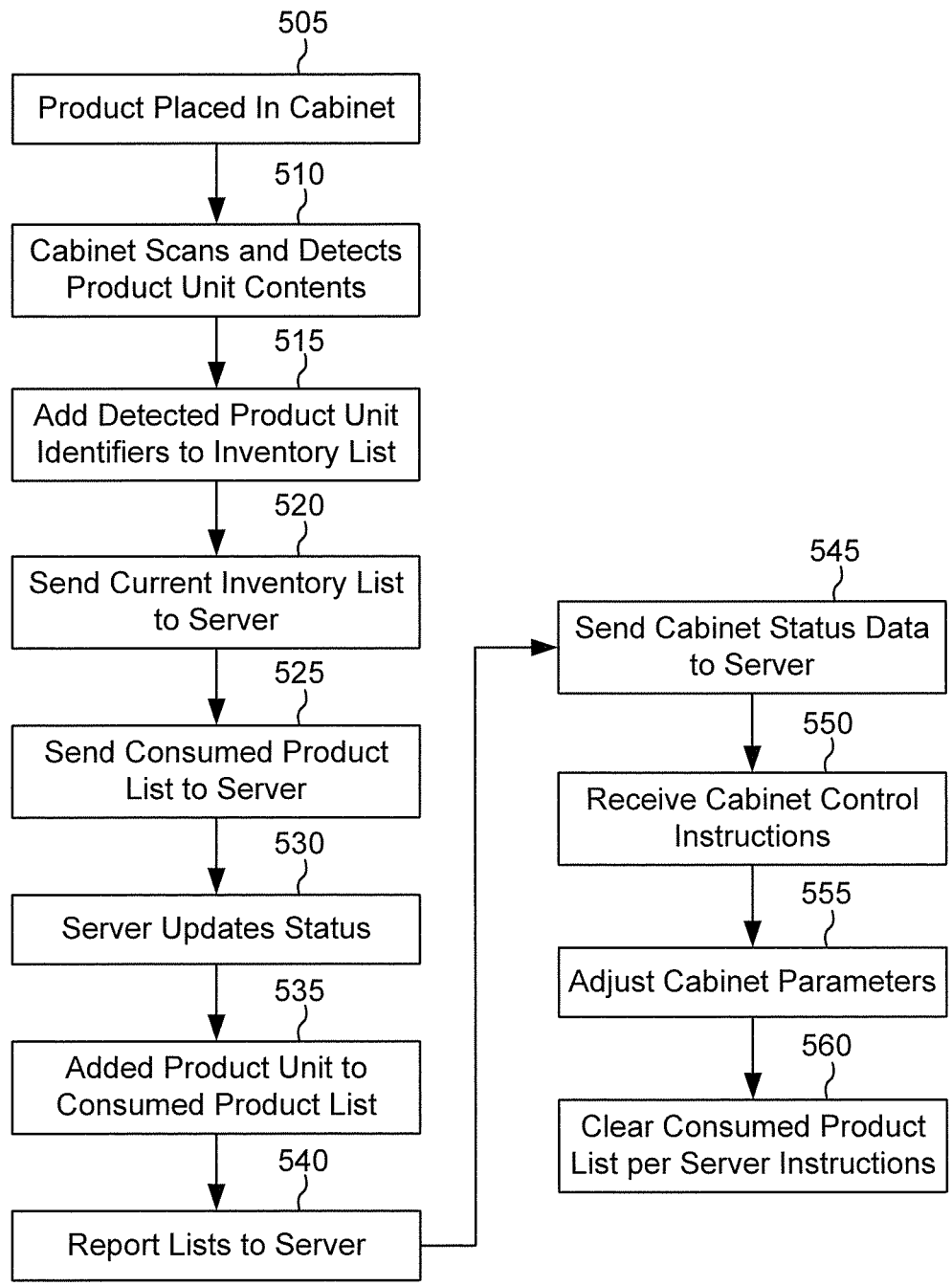
FIG. 5 depicts a flowchart of a second process in accordance with a disclosed embodiment.

FIG. 5 depicts a flowchart of a second process in accordance with a disclosed embodiment. In this process, each cabinet 100 can again function as a "virtual warehouse" of product units 200 located at each product location, such as hospital pharmacies. This process is particularly useful when the product is not sold when shipped for placement in a cabinet, but rather is held on consignment in the cabinet.

In particular, the embodiments described can be used for high-dollar injectable pharmaceuticals, which a pharmacy may desire to have readily available but may not be willing or able to pre-purchase. In this case, the consignment product in the "virtual warehouse" cabinet functions to answer a significant and immediate need in the industry.

In a disclosed process, at some point product units 200 are delivered to and placed within cabinet 100 at a customer site (step 505). Cabinet 100 wirelessly scans its contents to detect the serial numbers of the RFID tags of each of the product units (step 510), and add those to the current inventory list (step 515). Cabinet 100 will communicate the current inventory list to server system 310 (step 520). Cabinet 100 will also communicate the consumed inventory list to server system 310 (step 525). Server system 310 will update a status record for each corresponding serial number (step 530).

Cabinet 100 continues to periodically wirelessly scan its contents as in step 505 above. When the cabinet 100 no longer detects a given RFID serial number of a product unit 200, that serial number is added to the consumed product list (step 535), and can be removed from the current inventory list. The consumed list and updated current inventory list are eventually reported to server system 310, as described above (step 540). Typically, this will be when the product unit 100 is opened and the product is consumed, but it can also happen when the RFID tag is destroyed when the packaging is opened, or if the product is otherwise removed, stolen, destroyed, etc.

In some embodiments, a particular product unit is not moved to the consumed product list immediately when it is not detected, but only when it has not been detected for a significant period, such as 24, 48, or 72 hours. This is to accommodate the event that the product unit 200 is removed from cabinet 100 in anticipation of use, but is not actually consumed, and so is returned to the cabinet 100 and is thereafter detected by cabinet 100.

In some embodiments, the temperature and other parameters of the cabinet 100 can be directly modified by cabinet data processing system 150. Further, server system 310 can send appropriate commands to cabinet data processing system 150 to change the cabinet parameters. In this way, for example, server system 310 can determine the optimal cabinet parameters according to the current cabinet inventory, and thereafter modify the parameters accordingly. Cabinet 100 sends cabinet status data to server system 310 (step 545) indicating the current status of the cabinet and inventory, such as that determined by any sensor devices 140. Cabinet 100 receives cabinet control instructions from server 310 (step 550), and adjusts the cabinet parameters accordingly (step 555).

In various embodiments, a cabinet's current inventory list is reconstructed each time the cabinet scans its contents. The consumed inventory list is not routinely cleared by the cabinet until its contents have been sent to the server system. In some embodiments, the cabinet will receive an instruction from the server to clear the consumed inventory list, and will do so (step 560).

The systems and techniques described herein, while particularly described in a pharmaceutical context, are of course not limited to pharmaceuticals. Those of skill in the art will recognize that these techniques can be applied to any number of other products, with particular utility in managing inventory of consumable products such as drugs, foods, drinks, liquors, etc.

Those skilled in the art will recognize that, for simplicity and clarity, the full structure and operation of all systems suitable for use with the present disclosure is not being depicted or described herein. Instead, only so much of a data processing system as is unique to the present disclosure or necessary for an understanding of the present disclosure is depicted and described. The remainder of the construction and operation of these systems may conform to any of the various current implementations and practices known in the art.

It is important to note that while the present disclosure has been described in the context of a fully functional system, those skilled in the art will appreciate that at least portions of the mechanism of the present disclosure are capable of being distributed in the form of a instructions contained within a machine usable medium in any of a variety of forms, and that the present disclosure applies equally regardless of the particular type of instruction or signal bearing medium utilized to actually carry out the distribution. Examples of machine usable mediums include: nonvolatile, hard-coded type mediums such as read only memories (ROMs) or erasable, electrically programmable read only memories (EEPROMs), user-recordable type mediums such as floppy disks, hard disk drives and compact disk read only memories (CD-ROMs) or digital versatile disks (DVDs), and transmission type mediums such as digital and analog communication links.

Although an exemplary embodiment of the present disclosure has been described in detail, those skilled in the art will understand that various changes, substitutions, variations, and improvements of the subject matter disclosed herein may be made without departing from the spirit and scope of the disclosure in its broadest form.

None of the description in the present application should be read as implying that any particular element, step, or function is an essential element which must be included in the claim scope: THE SCOPE OF PATENTED SUBJECT MATTER IS DEFINED ONLY BY THE ALLOWED CLAIMS. Moreover, none of these claims are intended to invoke paragraph six of 35 USC § 112 unless the exact words "means for" are followed by a participle.

What is claimed is:

1. A product inventory management system comprising:
   a cabinet configured to contain a plurality of pharmaceutical product units having radio frequency identifier (RFID) tags, the cabinet further configured to monitor the pharmaceutical product units by wirelessly detecting the RFID tags; and
   a server system configured to communicate over a network with the cabinet, the server system configured to manage contents of the cabinet, the server system configured to initiate an order to have additional pharmaceutical product units added to the cabinet according to a current inventory list for the cabinet;
   wherein the pharmaceutical product units in the cabinet include consignment pharmaceutical product units,
   wherein the server system is configured to (i) maintain one or more of the pharmaceutical product units on the current inventory list for at least a predetermined time period after removal of the one or more pharmaceutical product units from the cabinet, and (ii) remove the one or more pharmaceutical product units from the current inventory list following an expiration of at least the predetermined time period after the removal of the one or more pharmaceutical product units from the cabinet, and wherein the server system is configured to create an invoice in response to removal of at least one of the pharmaceutical product units from the current inventory list.

2. The product inventory management system of claim 1, wherein the server system is configured to create the invoice at a time of the removal of the at least one pharmaceutical product unit from the current inventory list.

3. The product inventory management system of claim 1, wherein the server system is configured to create the invoice at a time after the removal of the at least one pharmaceutical product unit from the current inventory list.

4. The product inventory management system of claim 1, wherein the predetermined time period is at least 24 hours.

5. The product inventory management system of claim 1, wherein the server system is configured to not remove the one or more pharmaceutical product units from the current inventory list when the one or more pharmaceutical product units are returned to the cabinet within the predetermined time period after the removal of the one or more pharmaceutical product units from the cabinet.

6. The product inventory management system of claim 1, wherein the server system comprises a plurality of servers.

7. The product inventory management system of claim 1, wherein the cabinet is a first cabinet, and wherein the product inventory management system further comprises:
  a second cabinet configured to contain a plurality of second pharmaceutical product units having second RFID tags, the second cabinet configured to monitor the second pharmaceutical product units by wirelessly detecting the second RFID tags, and
  wherein the server system is configured to communicate over the network with the second cabinet, the server system configured to manage contents of the second cabinet.

8. A product inventory management system comprising:
  a first cabinet and a second cabinet, wherein each cabinet is configured to contain a plurality of pharmaceutical product units having radio frequency identifier (RFID) tags, each cabinet further configured to monitor the pharmaceutical product units in that cabinet by wirelessly detecting the RFID tags; and
  a server system configured to communicate over a network with the first cabinet and the second cabinet, the server system configured to manage contents of at least one of the first cabinet and the second cabinet, the server system configured to create an order to have additional pharmaceutical product units added to the at least one cabinet according to a current inventory list for the at least one cabinet,
  wherein the pharmaceutical product units in the at least one of the first cabinet and the second cabinet include consignment pharmaceutical product units,
  wherein the server system is configured to (i) maintain one or more of the pharmaceutical product units on the current inventory list for at least a predetermined time period after removal of the one or more pharmaceutical product units from the at least one cabinet, and (ii) remove the one or more pharmaceutical product units from the current inventory list following an expiration of at least the predetermined time period after the removal of the one or more pharmaceutical product units from the at least one cabinet, and the server system is configured to create an invoice in response to removal of at least one of the pharmaceutical product units from the current inventory list.

9. The product inventory management system of claim 8, wherein the server system is configured to create the invoice at a time of the removal of the at least one pharmaceutical product unit from the current inventory list.

10. The product inventory management system of claim 8, wherein the server system is configured to create the invoice at a time after the removal of the at least one pharmaceutical product unit from the current inventory list.

11. The product inventory management system of claim 8, wherein the predetermined time period is at least 24 hours.

12. The product inventory management system of claim 8, wherein the server system is configured to not remove the one or more pharmaceutical product units from the current inventory list when the one or more pharmaceutical product units are returned to the at least one cabinet within the predetermined time period after the removal of the one or more pharmaceutical product units from the at least one cabinet.

13. The product inventory management system of claim 8, wherein the server system comprises a plurality of servers.

14. A product inventory management system comprising:
  a cabinet configured to contain a plurality of pharmaceutical product units on consignment, each of the plurality of consignment pharmaceutical product units having a radio frequency identifier (RFID) tag, the cabinet further configured to monitor the consignment pharmaceutical product units by wirelessly detecting the RFID tags; and
  at least one server configured to communicate over a network with the cabinet, the at least one server configured to manage contents of the cabinet, the at least one server configured to create an order to have additional consignment pharmaceutical product units added to the cabinet according to a current inventory list for the cabinet,
  wherein the at least one server is configured to (i) determine when at least a predetermined time period has elapsed following removal of a first of the consignment pharmaceutical product units from the cabinet, and (ii) identify the first consignment pharmaceutical product unit as consumed for invoicing following expiration of at least the predetermined time period after the first consignment pharmaceutical product unit is removed from the cabinet.

15. The product inventory management system of claim 14, wherein the at least one server is configured to create an invoice at a time of removal of the first consignment pharmaceutical product unit from the current inventory list.

16. The product inventory management system of claim 14, wherein the at least one server is configured to create an invoice after removal of the first consignment pharmaceutical product unit from the current inventory list.

17. The product inventory management system of claim 14, wherein the at least one server is configured to remove the first consignment pharmaceutical product unit from the current inventory list following the expiration of at least the predetermined time period after removal of the first consignment pharmaceutical product unit from the cabinet.

18. The product inventory management system of claim 14, wherein the predetermined time period is at least 24 hours.

19. The product inventory management system of claim 14, wherein the at least one server is configured to not remove the first consignment pharmaceutical product unit from the current inventory list when the first consignment pharmaceutical product unit is returned to the cabinet within the predetermined time period after removal of the first consignment pharmaceutical product unit from the cabinet.

20. The product inventory management system of claim 14, wherein the at least one server comprises a system of servers.

21. The product inventory management system of claim 14, wherein the cabinet is a first cabinet, and wherein the product inventory management system further comprises:
   a second cabinet configured to contain a second plurality of pharmaceutical product units on consignment, each of the second plurality of consignment pharmaceutical product units having a second RFID tag, the second cabinet configured to monitor the second plurality of consignment pharmaceutical product units by wirelessly detecting the second RFID tags, and
   wherein the at least one server is configured to communicate over the network with the second cabinet, the at least one server configured to manage contents of the second cabinet.

22. A product inventory management system comprising:
   a first cabinet and a second cabinet, wherein the first cabinet is configured to contain a first plurality of pharmaceutical product units on consignment and the second cabinet is configured to contain a second plurality of pharmaceutical product units on consignment, each consignment pharmaceutical product unit of the first and second plurality of consignment pharmaceutical product units having a radio frequency identifier (RFID) tag, the first cabinet configured to monitor the first plurality of consignment pharmaceutical product units by wirelessly detecting the RFID tags of the first plurality of consignment pharmaceutical product units and the second cabinet configured to monitor the second plurality of consignment pharmaceutical product units by wirelessly detecting the RFID tags of the second plurality of consignment pharmaceutical product units; and
   at least one server configured to communicate over a network with the first cabinet and the second cabinet, the at least one server configured to manage contents of the first cabinet based on a first current inventory list and contents of the second cabinet based on a second current inventory list, the at least one server configured to create an order to have additional consignment pharmaceutical product units added to at least one of the first and second cabinets according to at least one of the first and second current inventory lists,
   wherein the at least one server is configured to (i) determine when at least a predetermined time period has elapsed following removal of a specified one of the first plurality of consignment pharmaceutical product units from the first cabinet, and (ii) identify the specified consignment pharmaceutical product unit as consumed for invoicing following expiration of at least the predetermined time period after the specified consignment pharmaceutical product unit is removed from the first cabinet.

23. The product inventory management system of claim 22, wherein the at least one server is configured to create an invoice at a time of removal of the specified consignment pharmaceutical product unit from the first current inventory list.

24. The product inventory management system of claim 22, wherein the at least one server is configured to create an invoice at a time after removal of the specified consignment pharmaceutical product unit from the first current inventory list.

25. The product inventory management system of claim 22, wherein the at least one server is configured to remove the specified consignment pharmaceutical product unit from the first current inventory list following the expiration of at least the predetermined time period after removal of the specified consignment pharmaceutical product unit from the first cabinet.

26. The product inventory management system of claim 22, wherein the predetermined time period is at least 24 hours.

27. The product inventory management system of claim 22, wherein the at least one server is configured to not remove the specified consignment pharmaceutical product unit from the first current inventory list when the specified consignment pharmaceutical product unit is returned to the first cabinet within the predetermined time period after removal of the specified consignment pharmaceutical product from the first cabinet.

28. The product inventory management system of claim 22, wherein the at least one server comprises a system of servers.

* * * * *